(12) United States Patent
Kiyomine et al.

(10) Patent No.: US 7,211,116 B2
(45) Date of Patent: May 1, 2007

(54) HAIR DYE COMPOSITION

(75) Inventors: Akira Kiyomine, Tokyo (JP); Masaki Fukuhara, Tokyo (JP); Masayoshi Nojiri, Tokyo (JP); Hideyuki Abe, Wakayama (JP); Masakatsu Takahashi, Wakayama (JP); Hiromoto Mizushima, Wakayama (JP)

(73) Assignee: Kao Corporation, Tokyo (JP)

( * ) Notice: Subject to any disclaimer, the term of this patent is extended or adjusted under 35 U.S.C. 154(b) by 302 days.

(21) Appl. No.: 10/497,538

(22) PCT Filed: Dec. 13, 2002

(86) PCT No.: PCT/JP02/13068

§ 371 (c)(1),
(2), (4) Date: Dec. 27, 2004

(87) PCT Pub. No.: WO03/051322

PCT Pub. Date: Jun. 26, 2003

(65) Prior Publication Data
US 2005/0102770 A1    May 19, 2005

(30) Foreign Application Priority Data
Dec. 14, 2001  (JP) .............. 2001-380949
May 10, 2002  (JP) .............. 2002-135939

(51) Int. Cl.
*A61K 7/13* (2006.01)
(52) U.S. Cl. .............. 8/405; 8/406; 8/407; 8/455; 8/568; 8/574; 8/597; 8/602; 8/101; 8/111; 548/400
(58) Field of Classification Search .......... 8/405, 8/406, 407, 455, 568, 574, 597, 602, 101, 8/111; 548/400
See application file for complete search history.

(56) References Cited
U.S. PATENT DOCUMENTS
6,613,313 B2 * 9/2003 Kimura ............ 424/70.1

FOREIGN PATENT DOCUMENTS

| EP | 806 198 | 11/1997 |
|----|---------|---------|
| FR | 2807650 | 10/2001 |
| FR | 2817474 | 6/2002 |
| JP | 2002-255759 | 9/2002 |

OTHER PUBLICATIONS
STIC Search Report Dated Oct. 2, 2006.*

* cited by examiner

Primary Examiner—Eisa Elhilo
(74) Attorney, Agent, or Firm—Oblon, Spivak, McClelland, Maier & Neustadt, P.C.

(57) ABSTRACT

Provided are a hair bleach composition, hair dye composition and a hair treatment additive having excellent bleaching power, capable of dyeing the hair with a bright and good color, and less damaging to the hair and less irritating to the scalp.

Described specifically, they are a two-part hair bleach composition, which contains (a) a nitrogenous compound represented by the following formula (1) or (2):

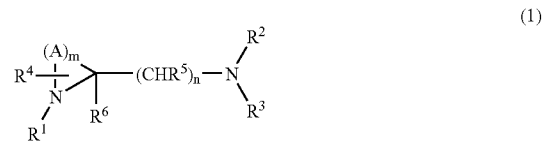

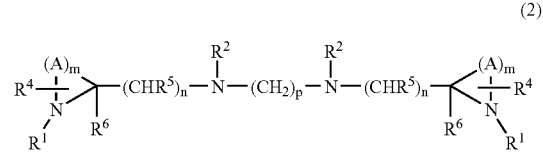

or salt thereof, or (A) a nitrogenous compound having a solubility parameter log P in octanol/water ranging from −1 to 4 and a hydrogen peroxide remaining ratio of from 5 to 90%, or salt thereof, (b) an oxidizing agent, and optionally (c) an alkali agent and, after mixing, has a pH of from 7.5 to 12; a two-part hair dye composition comprising (a) or (A), (b) and (c) and further (d) an oxidation dye or direct dye; and an additive used therefor.

30 Claims, No Drawings

HAIR DYE COMPOSITION

FIELD OF THE INVENTION

The present invention relates to a hair bleach composition and hair dye composition, each being less damaging to the hair and less irritating to the scalp during and after treatment therewith and at the same time, having excellent bleaching power and dyeing power; and an additive to be used for these compositions.

BACKGROUND OF THE INVENTION

For hair bleaching or dyeing, two-part bleaches or permanent hair dyes composed of a first component part containing an alkali agent and a second component part containing an oxidizing agent have been used widely. The oxidizing agent of the second component part is added in order to heighten the hair dyeing effect by utilizing the coupling reaction of an intermediate for an oxidation dye and at the same time, cause the hair to turn bright color by promoting oxidative decomposition of melanin granules in the hair. The alkali agent of the first component part is added in order to activate the oxidizing agent and thereby enhance the hair dyeing and bleaching effects. Not only to bleach the hair into a lighter color than the original color but also to dye the hair into a color different therefrom, it is necessary to bleach melanin and the other pigments sufficiently. The hair bleaching power usually depends on the amounts of the alkali and oxidizing agent. When the composition is used for such a purpose, both alkali and oxidizing agents must be incorporated in sufficient amounts.

It is the common practice to use ammonia or organic amine as the alkali agent and hydrogen peroxide as the oxidizing agent. Addition of these agents in a large amount to obtain necessary bleaching power, however, tends to cause damage to the hair or irritate the scalp, depending on their using amount.

As a conventional method for overcoming the above-described problem, provided are the use of 1,3-propanediamine (Japanese Patent Laid-Open No. Hei 5-246827), use of triazacyclononane (Japanese Patent Laid-Open No. 2002-255763), and the like. They however include the problem that in a mixture system for practical use, they cannot bring about satisfactory results in performance.

The present invention therefore provides a hair bleach composition and a hair dye composition, each having an excellent dyeing power, capable of dyeing the hair into beautiful bright color, and is less damaging to the hair and less irritating to the scalp.

Further, the present invention provides a novel additive to be incorporated for attaining the above-described object.

SUMMARY OF THE INVENTION

In the present invention, there is thus provided a hair bleach composition to be used after mixing a first component part containing an alkali agent and a second component part containing an oxidizing agent, which comprises, after mixing, the following components (a) to (c):

(a) a nitrogenous compound represented by the following formula (1) or (2), or salt thereof:

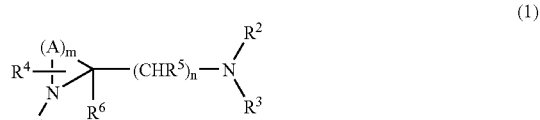

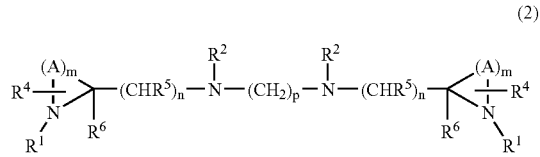

(wherein, one or two of As each represents $CH_2$ which may be substituted by one or two selected from O, S and NH, $R^1$ represents a hydrogen atom; an alkyl, cycloalkyl or alkenyl group which has 12 or less carbon atoms and may be substituted by at least one group selected from a hydroxy group, an amino group which may be substituted by at least one alkyl group, an amide group which may be substituted by at least one alkyl group, a $C_{1-6}$ (poly)alkoxy or benzyloxy group which may be substituted by a hydroxy or amino group, a thioether group and an ester group; an alkyl halide group; or a benzyl, pyridylmethyl or phenyl group which may be substituted by at least one halogen atom;

$R^2$ and $R^3$ each represents a hydrogen atom, an alkyl, alkenyl or cycloalkyl group which has 12 or less carbon atoms and may be substituted by at least one group selected from a hydroxy group, an amino group which may be substituted by at least one alkyl group and a $C_{1-6}$ alkoxy group; an acyl group having 12 or less carbon atoms, an alkylsulfonyl group having 12 or less carbon atoms, or a phenylsulfonyl group which may be substituted by at least one alkyl group; or $R^2$ and $R^3$ may form a 4- to 7-membered ring cyclic amino group together with a nitrogen atom adjacent thereto, $R^4$, $R^5$ and $R^6$ each represents a hydrogen atom; a hydroxy group; an amino group; an alkyl ether group; or an alkyl or alkenyl group which has 12 or less carbon atoms and may be substituted by at least one group selected from a hydroxy group, and an amino group which may be substituted by at least one alkyl group, m stands for an integer of from 2 to 5, n stands for an integer of from 1 to 4 and p stands for an integer of from 2 to 6, (b) an oxidizing agent; and
(c) an alkali agent; and after mixing, has a pH of from 7.5 to 12.

In the present invention, there is also provided a hair dye composition to be used after mixing a first component part containing an alkali agent and a second component part containing an oxidizing agent, which comprises, after mixing, the following components (A) and (b) to (d);

(A) a nitrogenous compound having a solubility parameter log P in octanol/water ranging from −1 to 4, and a hydrogen peroxide remaining ratio ranging from 5 to 90%; or salt of the compound, (b) an oxidizing agent,
(c) an alkali agent, and
(d) an intermediate for an oxidation dye or a direct dye; and after mixing, has a pH of from 7.5 to 12.

In the present invention, there is also provided an additive, for attaining an excellent performance, to the above-described hair bleach composition or hair dye composition to be used after mixing a first component part containing an alkali agent and a second component part containing an oxidizing agent, which comprises a nitrogenous compound satisfying either one of the following conditions:

(i) a nitrogenous compound represented by the above-described formula (1) or (2), or salt thereof (condition of chemical structure), and (ii) a nitrogenous compound having a solubility parameter log P value in octanol/water ranging from −1 to 4 and a hydrogen peroxide remaining ratio of from 5 to 90%, or salt thereof (condition of physical properties).

By satisfying at least one of the above-described conditions relating to physical properties and chemical structure and thereby causing the alkali agent and oxidizing agent to act efficiently in the hair, the additive contributes to improvements in bleaching power and hair dyeing power. Accordingly, without lowering bleaching power and hair dyeing power, the amounts of the alkali agent and oxidizing agent can be decreased, leading to alleviation of the hair damage and irritation to the scalp. In other words, it is possible to improve hair bleaching or dyeing power without increasing the hair damage or irritation to the scalp.

DETAILED DESCRIPTION OF THE INVENTION

The present inventors have found that the above-described problem can be overcome by incorporating, in a hair bleach or a hair dye, a nitrogenous compound having predetermined physical properties or a nitrogenous compound having a predetermined structure.

For the nitrogenous compound of the present invention satisfying the condition of physical properties, the following two requirements are necessary.

The first requirement is a remaining ratio of hydrogen peroxide. The remaining ratio of hydrogen peroxide is determined by measuring the remaining amount of hydrogen peroxide in a virtual hair bleach composition after a predetermined time. The remaining ratio exceeding a predetermined value allows existence of hydrogen peroxide which can be used for hair bleaching or dyeing and promotes the hair bleaching action. The remaining ratio below a predetermined value, on the other hand, prevents excessive stabilization of hydrogen peroxide, whereby the oxidizing agent acts to emit adequate —$O_2H$ (perhydroxy anion). The hydrogen peroxide remaining ratio in the present invention is from 5% to 90%, preferably from 10 to 87%, more preferably 15 to 70% under the measurement conditions of the hydrogen peroxide remaining ratio which will be described later.

Compounds exhibiting a hydrogen peroxide remaining ratio at or above the lower limit 5% can suppress decomposition of hydrogen peroxide serving as an oxidizing agent, while compounds exhibiting a hydrogen peroxide remaining ratio not greater than the upper limit 90% promotes the action (emission of —$O_2H$ or the like) of hydrogen peroxide as an oxidizing agent, which contributes to the appearance of a bleaching effect.

The second requirement is a solubility parameter log P in octanol/water. This is an index of a lipophilicity/hydrophilicity balance of the compound. More specifically, log P is a distribution ratio of a substance between a 1-octanol phase and an aqueous phase at 25° C. and is defined by the following equation:

$$\log P = \log ((\text{Substance})_{octanol}/(\text{Substance})_{water})$$

(wherein, (Substance)$_{octanol}$ represents a mole concentration of the substance in the 1-octanol phase, while (Substance)$_{water}$ represents a mole concentration of the substance in the aqueous phase).

The smaller the log P value, the more hydrophilic the substance is. In the present invention, this balance is an important factor influencing the penetration into the hair.

The log P value can be determined by various methods such as measurement and calculation. In this application, utilized was the value "clog P" calculated by a computer soft program which will be described later.

As a result, it has been found that in order to exhibit the effects of the present application, the solubility parameter log P must be −1 or greater but not greater than 4 (from −1 to 4). The log P value is preferably from −1 to 3, more preferably from −1 to 2.5.

The compound having the log P of −1 or greater penetrates into the hair well, while that having the log P of 4 or less exhibits good solubility upon mixing and is not easily separated or precipitated.

Model compounds as described below can be given as the nitrogenous compounds satisfying the conditions of the present invention. The present invention will next be described based on these model compounds.

In these model compounds, a relationship between structure and performance as described below is recognized and it will also be an index for the selection or designing of the nitrogenous compound of the present invention.

1. Control of Hydrogen Peroxide Remaining Ratio

In order to cause adequate decomposition of hydrogen peroxide, the cyclic nitrogen in the compound represented by the formula (1) or (2) is preferably tertiary. More specifically, the compound of the formula (1) or (2) wherein $R^1$ does not represent a hydrogen atom is preferred, of which the compound of the formula (1) or (2) wherein $R^1$ represents an alkyl or alkenyl group is especially preferred.

The hydrogen peroxide remaining ratio in the present invention is measured in the following manner. Measurement of hydrogen peroxide remaining ratio %: In a 50 mL screw tube are charged 20.0 mg of Compound (A) and 5.98 g of deionized water to dissolve the former in the latter. To the resulting solution are added a 2.00 g portion of an aqueous Cu solution obtained by adding deionized water to 26.8 mg of $CuCl_2.2H_2O$ to give a total amount of 100 g, 2.00 g of 15% aqueous ammonia and 10.00 g of 2% aqueous hydrogen peroxide. A magnetic stirrer is put into the tube and the mixture therein is stirred for 10 minutes in a 30° C. water bath. Ten minutes later, 0.5 g of the resulting stirred solution is weighed precisely in a 200 mL Erlenmeyer flask with ground-in stopper. After addition thereto of 50 mL of a 10% aqueous solution of sulfuric acid, 10 mL of dichloromethane and 10 mL of a 10% aqueous solution of potassium iodide, the mixture is vigorously shaken and then allowed to stand in the dark for about 15 minutes. Then, the reaction mixture is titrated with a 0.02N aqueous solution of sodium thiosulfate. When the yellow color becomes pale during titration, 1 mL of 1% aqueous starch (suspension) is added. The point when a violet color (bluish violet to reddish violet) disappears completely is designated as a terminal point and hydrogen peroxide % is determined in accordance with the below-described equation. The amount of hydrogen peroxide in an aqueous solution obtained by diluting 10.00 of 2% aqueous hydrogen peroxide with 10.00 g of deionized water is also measured and the hydrogen peroxide amount at this time is taken as a hydrogen peroxide remaining ratio of 100%.

$$\text{Hydrogen peroxide amount \%} = \frac{\text{Titration amount (mL)} \times \text{titer of 0.02 N sodium thiosulfate} \times 0.34014}{\text{(Amount of stirred solution weighed (mg))}} \times 100$$

2. Control of Bleaching Activity

In order to improve bleaching activity, the amino group on the side chain in the formula (1) is preferably a primary or tertiary one. In other words, it is preferred that at least one of $R^2$ and $R^3$ represents a hydrogen atom, and especially preferred that both represent a hydrogen atom.

3. Control of Solubility Parameter log P

The log P is a balance between hydrophilicity and lipophilicity so that compounds may be selected or designed in consideration of its balance in the whole compound.

Examples of a measure for improving lipophilicity include introduction of a lipophilic group such as hydrocarbon and a reduction in the hydrophilic moiety. More specifically, lipophilicity is improved by introducing a hydrocarbon group into $R^4$, $R^5$ and/or $R^6$.

Examples of a measure for improving hydrophilicity include introduction of a hetero atom and, in a hydrocarbon atom, substitution of the hydrogen atom of the alkyl group or alkylene group with a group having a hydrophilic moiety such as aminoalkyl group or hydroxy group.

In the present invention, the solubility parameter log P is calculated using a computer software program. Calculation of log P: The Partition Coefficient (Octanol/Water)–C log P of CS Chem3D ver. 6.0 (product of Cambridge Soft) was used. Instead of salt compounds such as amine hydrochloride or sodium carboxylate salt, the corresponding amine or carboxylic acid ($CO_2H$) was input upon calculation.

Examples of the nitrogenous compound or salt thereof capable of satisfying the conditions of physical properties, that is, a solubility parameter log P value in octanol/water ranging from −1 to 4 and a hydrogen peroxide remaining ratio ranging from 5 to 90% include 2-aminoethyl-1-methylpyrrolidine, 2-aminomethyl-1-ethylpyrrolidine, 2-aminomehtyl-1-butylpyrrolidine, 2-aminomethyl-1-hydroxyethylpyrrolidine, 2-N-ethylaminomethyl-1-ethylpyrrolidine and 1-ethyl-2-(N-hydroxyethyl)aminomethylpyrrolidine.

The log P value and hydrogen peroxide remaining ratio of some compounds of the present invention capable of satisfying the above-described conditions are shown in Table 1, together with those of the conventional art.

TABLE 1

|  | Compound Name | Purchased from, or purity (GC area %) | LogP Value | Hydrogen peroxide remaining ratio |
|---|---|---|---|---|
| Example Compound | 2-Aminomethyl-1-hydroxyethylpyrrolidine | 98.6 | −0.35 | 85.1 |
|  | 2-Aminomethyl-1-methylpyrrolidine | 99.4 | 0.31 | 63.1 |
|  | 1-Ethyl-2-(N-hydroxyethyl)aminomethylpyrrolidine | 99.0 | 0.66 | 30.5 |
|  | 2-Aminomethyl-1-ethylpyrrolidine | 98.8 | 0.84 | 43.4 |
|  | 2-N-Ethylaminomethyl-1-ethylpyrrolidine | 99.4 | 1.53 | 32.9 |
|  | 2-Aminomethyl-1-butylpyrrolidine | 98.2 | 1.9 | 45.3 |
|  | 2-Aminomethyl-1-cyclohexylpyrrolidine | 94.6 | 2.12 | 17.0 |
| Comparative Compound | Ethylenediaminetetraacetic acid | Wako Pure Chemical (2Na salt) | −1.93 | 100 |
|  | Monoethanolamine | Wako Pure Chemical | −1.3 | 5.9 |
|  | Diethanolamine | Tokyo Kasei | −1.46 | 2.9 |
|  | 1,4,7-Triazacyclononane | Tokyo Kasei (3HCl salt) | −2.23 | 96.6 |
|  | 1,4,7-Trimethyl-1,4,7-triazacyclononane | Aldrich | −1.23 | 64.8 |
|  | 1,3-Propanediamine | Tokyo Kasei | −1.49 | 19.3 |
|  | 2-Hydroxy-1,3-propanediamine | Tokyo Kasei | −2.05 | 33.6 |

Based on the above-described finding, it has also been found in the invention that the compounds represented by the formula (1) or (2), and salts thereof are also effective for hair bleaching.

In the formulas (1) and (2), A constituting a ring is composed principally of —$CH_2$— and in some cases, it may have, instead of one or two —$CH_2$—, —O—, —S— and/or —NH—.

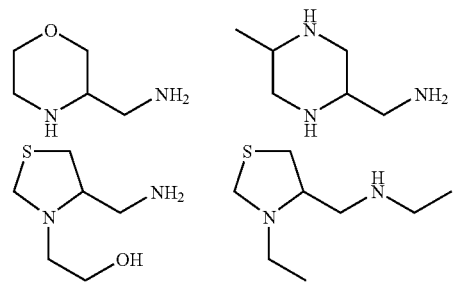

In the formulas (1) and (2), $R^1$ represents a hydrogen atom; an alkyl, cycloalkyl, alkenyl, aminoalkyl, hydroxyalkyl, alkoxyalkyl, thioetheralkyl, amide-substituted alkyl or ester-substituted alkyl group, each having 12 or less, preferably 6 or less carbon atoms; an alkyl halide group having 12 or less carbon atoms; a benzyl or phenyl group which may be substituted by a halogen atom; and a cyclic aminoalkyl group. Examples of the alkyl group having 12 or less carbon atoms include methyl, ethyl, propyl, butyl, pentyl, hexyl, isopropyl, isobutyl, and isopentyl group. As $R^1$, preferred is an alkyl or alkenyl group having 1 to 6 carbon atoms, with methyl, ethyl, butyl or hydroxyethyl group being especially preferred from the viewpoints of bleaching power·dyeing power.

In the formulas (1) and (2), $R^2$ and $R^3$ each represents a hydrogen atom; an alkyl, alkenyl, hydroxyalkyl, aminoalkyl, acyl or alkylsulfonyl group having 12 or less, preferably 1 to 6 carbon atoms; a phenylsulfonyl group; or a cyclic amino group, of which alkyl, hydroxyalkyl or alkenyl group having 12 or less carbon atoms is preferred, with a methyl, ethyl or hydroxyethyl group being more preferred from the viewpoints of bleaching power·dyeing power. It is especially preferred that at least one of $R^2$ and $R^3$ represents a hydrogen atom, and most preferred that both represent a hydrogen atom.

In the formulas (1) and (2), $R^4$, $R^5$ and $R^6$ each represents a hydrogen atom; a hydroxy group; and an alkyl, alkenyl, hydroxyalkyl or aminoalkyl group having 12 or less carbon atoms, of which alkyl or alkenyl group having 12 or less, especially 1 to 6 carbon atoms is preferred. The methyl or ethyl group is especially preferred from the viewpoint of the bleaching power·dyeing power. It is more preferred that any one of $R^4$, $R^5$ and $R^6$ represents a hydrogen atom, and most preferred that $R^6$ represents a hydrogen atom.

Each functional group will next be described more specifically.

In the formulas (1) and (2), examples of the alkyl or alkenyl group having 12 or less carbon atoms, which is represented by $R^1$, $R^2$, $R^3$, $R^4$, $R^5$ or $R^6$, include methyl, ethyl, propyl, butyl, pentyl, hexyl, isopropyl, isobutyl, isopentyl, vinyl and allyl groups, with methyl and ethyl groups being especially preferred from the viewpoint of bleaching power·dyeing power.

In the formulas (1) and (2) examples of the aminoalkyl group having 12 or less carbon atoms, which is represented by $R^1$, $R^2$, $R^3$, $R^4$, $R^5$ or $R^6$, include aminomethyl, aminoethyl, aminopropyl, aminobutyl, aminopentyl and aminohexyl groups, with aminomethyl, aminoethyl and aminopropyl groups are preferred.

In the formulas (1) and (2), the poly(alkoxy) group represented by $R^1$ means a polyalkoxy group to which an alkoxy or alkyleneoxide has been linked.

In the formulas (1) and (2), examples of the acyl group having 12 or less carbon atoms, which is represented by $R^2$ or $R^3$, include formyl, acetyl, propionyl, butanoyl, pentanoyl and hexanoyl groups, with acetyl and propionyl groups being especially preferred.

In the formulas (1) and (2), examples of the alkylsulfonyl group having 12 or less carbon atoms, which is represented by $R^2$ or $R^3$, include methanesulfonyl and ethanesulfonyl groups.

In the formulas (1) and (2), examples of the phenylsulfonyl group which may be substituted by an alkyl group, which is represented by $R^2$ or $R^3$, include phenylsulfonyl and tosyl groups.

In the formulas (1) and (2), examples of the 4- to 7-membered ring cyclic amino group which may be formed by coupling of $R^2$ and $R^3$ include pyrrolidinyl, piperidino and piperazinyl groups.

In the formulas (1) and (2), examples of the amino group which may be substituted by at least one alkyl group having 12 or less carbon atoms, which is represented by $R^1$, $R^2$, $R^3$ or $R^4$, include amino, methylamino, dimethylamine, ethylamino and diethylamino groups.

In the formulas (1) and (2), examples of the $C_{1-6}$ alkoxy group which may be substituted for an alkyl group as $R^1$ having 12 or less carbon atoms include methoxy, ethoxy, propyloxy, isopropyloxy and butoxy groups, of which methoxy) and ethoxy groups are preferred.

In the formulas (1) and (2), examples of the benzyl group as $R^1$ which may be substituted by a halogen atom include benzyl, chlorobenzyl, bromobenzyl and dichorobenzyl groups, with benzyl group being especially preferred. Examples of the phenyl group which may be substituted by a halogen atom include phenyl, chlorophenyl, bromophenyl and dichlorophenyl groups, with a phenyl group being especially preferred.

In the formulas (1) and (2), the integer m is preferably 2 to 4, with 3 being especially preferred. The integer n stands for 1 to 4, of which 1 or 2 is preferred and 1 is especially preferred. The integer p is especially preferred from the viewpoint of bleaching power·dyeing power when it stands for 2 or 3.

In one preferred embodiment of the present invention, a compound effective for hair bleaching is a cyclic amine compound represented by the following formula (1a) or (2a):

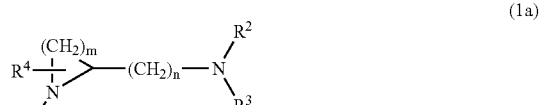

(1a)

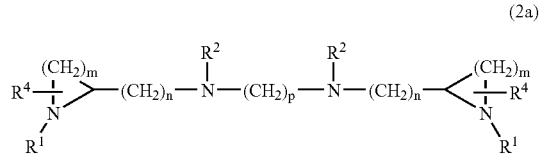

(2a)

(wherein, $R^1$ represents a hydrogen atom; an alkyl, cycloalkyl or alkenyl group which has 12 or less carbon atoms and may be substituted by at least one group selected from a hydroxy group, an amino group which may be substituted by at least one alkyl group, an amide group which may be substituted by at least one alkyl group, a $C_{1-6}$ (poly)alkoxy or benzyloxy group which may be substituted by a hydroxy or amino group, a thioether group and an ester group; an alkyl halide group, or a benzyl, pyridylmethyl or phenyl group which may be substituted by at least one halogen atom;

$R^2$ and $R^3$ each represents a hydrogen atom, a $C_{1-6}$ alkyl group which may substituted by an amino group which may be substituted by at least one hydroxy or alkyl group; a $C_{1-6}$ acyl group; a $C_{1-6}$ alkylsulfonyl group; or a phenylsulfonyl group which may be substituted by an alkyl group; or $R^2$ and $R^3$ may form a 4- to 7-membered ring cyclic amino group together with a nitrogen atom adjacent thereto, $R^4$ represents a hydrogen atom; or a $C_{1-6}$ alkyl group which may be substituted by an amino group which may be substituted by at least one hydroxy or alkyl group, m stands for an integer of from 2 to 5, n stands for an integer of from 1 to 4 and p stands for an integer of from 2 to 6).

These cyclic amine compounds (1a) and (2a) are known compounds and can be prepared, for example, by the process as described in Japanese Patent Publication No. Sho 46-37589, Japanese Patent Publication No. Sho 48-13551, Japanese Patent Publication No. Sho 49-24067, Japanese Patent Publication No. Sho 54-7792, Japanese Patent Publication No. Sho 46-27457, Japanese Patent Publication No. Sho 60-56706, International Publication No. 87/07271 pamphlet, and Japanese Patent Publication No. Hei 7-103098.

The cyclic amine compound (1a) may be in the form of an optically active (S) form or (R) form, or any mixture thereof. The cyclic amine compound (2a) may be any diastereomer or a mixture thereof at any ratio. Specific examples of the cyclic amine compounds (1a) and (2a) will next be shown.

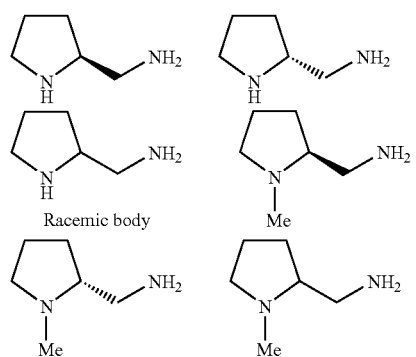

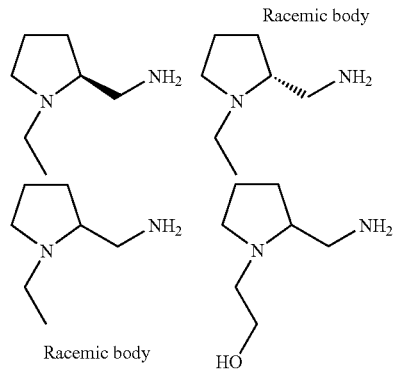

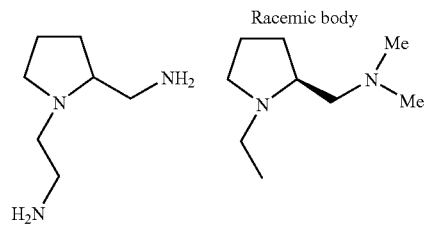

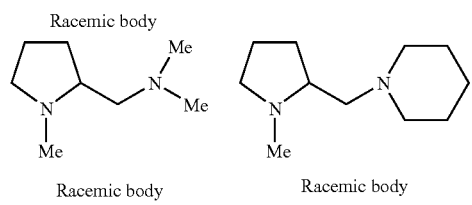

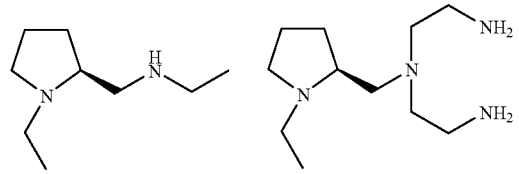

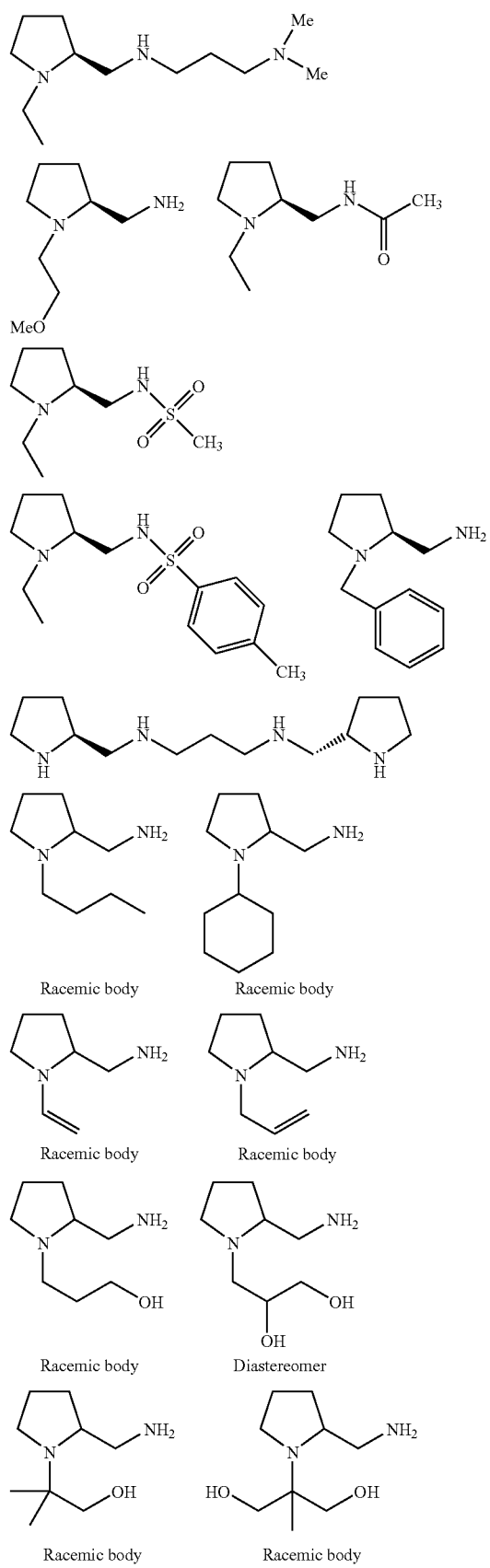

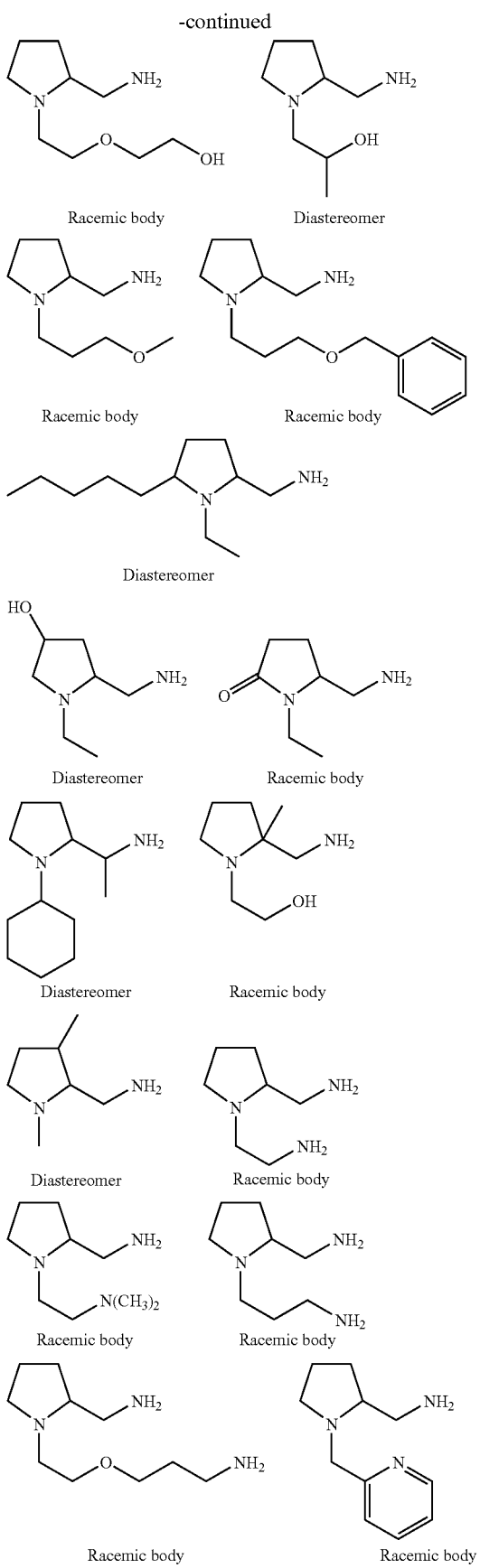

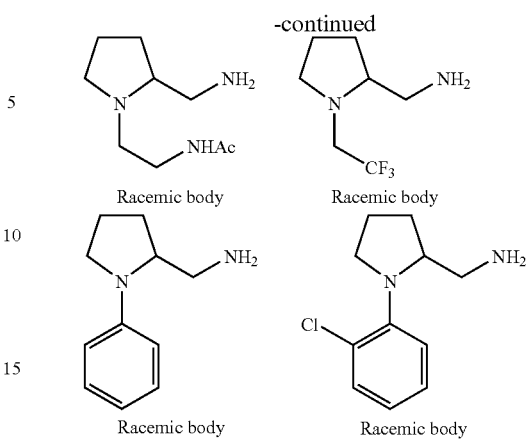

In another preferred embodiment of the present invention, a compound effective for hair bleaching is a 2-aminomethylpyrrolidine derivative represented by the following formula (1b):

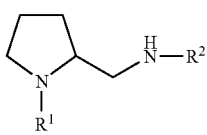
(1b)

(in the formula (1b), $R^1$ and $R^2$ each represents a $C_{1-6}$ alkyl or $C_{3-6}$ cycloalkyl group which may be substituted by at least one group selected from hydroxy group, tertiary amino groups and $C_{1-6}$ alkoxy groups).

The above-described 2-aminomethylpyrrolidine derivative is a novel compound. The compound can be prepared, for example, in the following manner:

A proline derivative represented by the following formula (3):

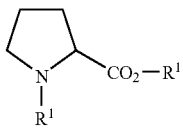
(3)

(in the formula (3), two $R^1$s may be the same or different and each represents a $C_{1-6}$ alkyl or $C_{3-6}$ cycloalkyl group which may be substituted by at least one group selected from hydroxy group, tertiary amino groups and $C_{1-6}$ alkoxy groups) is caused to react with a primary amine compound represented by the following formula (4):

  (4)

(in the formula (4), $R^2$ represents a $C_{1-6}$ alkyl or $C_{3-6}$ cycloalkyl group which may be substituted by at least one group selected from hydroxy group, tertiary amino groups and $C_{1-6}$ alkoxy groups) to obtain an amidated proline derivative represented by the following formula (5):

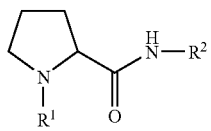

(5)

(in the formula (5), $R^1$ and $R^2$ each has the same meaning as described above), followed by reduction of the amide group with a reducing agent.

In the amidation step, the primary amine (4) is used in an amount ranging from 0.5 to 20 equivalents relative to the raw material proline derivative (4). As a catalyst, alcoholate such as sodium methoxide (NaOMe), iodine ion such as sodium iodide and cyan ion such as sodium cyanide may be added. As the reaction solvent, solvents ordinarily employed in organic synthesis, for example, an alcohol solvent such as methanol, halogen solvent such as chloroform, aromatic solvent such as benzene, ether solvent such as diethyl ether, hydrocarbon solvent such as hexane, acetonitrile, DMF, DMSO, N-methylpyrrolidone or water, or mixture thereof may be used. The reaction can be effected within a temperature range of from 0 to 220° C. The reaction is usually carried out under normal pressure.

In the reduction step, a hydrogenation reagent may be used as the reducing agent. Examples include $LiAlH_4$ and $NaAlH_4$. The amount of the hydrogenation reagent falls within a range of from 0.5 to 20 equivalents relative to the amidated proline derivative represented by the formula (5). The reduction is conducted in an inert solvent, for example, an aromatic solvent such as benzene, an ether solvent such as diethyl ether, or hydrocarbon solvent such as hexane. The reaction is effected within a range of from −20° C. to reflux temperature.

The aminomethylpyrrolidine derivative (1b) has at least one asymmetric hydrocarbon. Each asymmetric hydrocarbon may be an optically active substance or racemic body, or a mixture thereof at any ratio. In view of a production cost, a racemic body or a mixture of diastereomers at any ratio is preferred.

Specific examples of the aminomethylpyrrolidine derivative (1b) include the compounds represented by the following chemical structures:

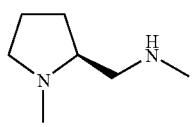 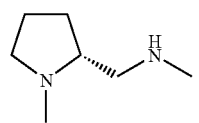

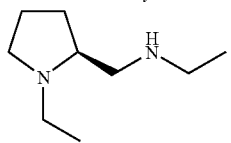
Racemic body

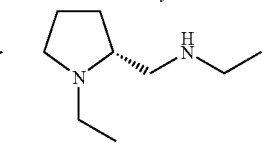
Racemic body

-continued

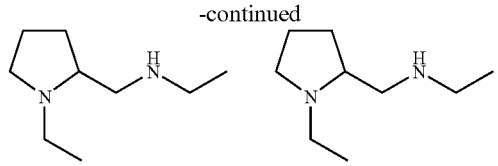

Racemic body      Racemic body

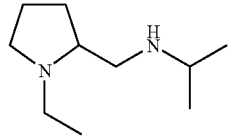

Racemic body

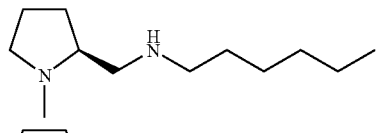

Racemic body

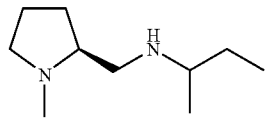

Racemic body

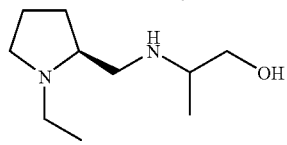

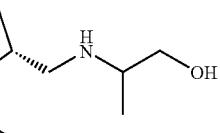

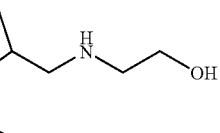

Racemic body

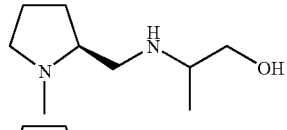

Racemic body

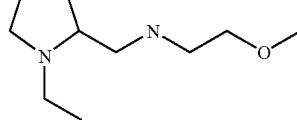

Racemic body

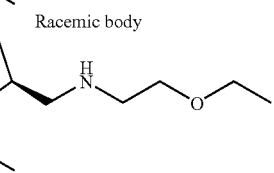

-continued
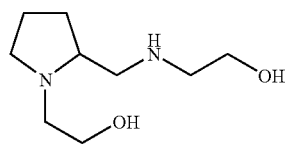
Racemic body
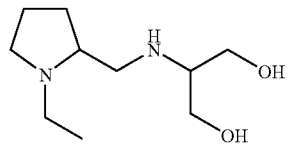
Racemic body
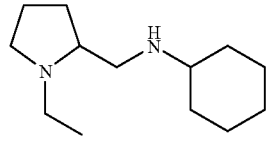
Racemic body
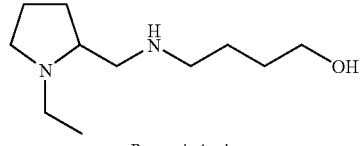
Racemic body
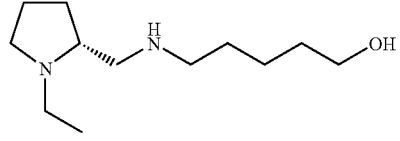
Racemic body
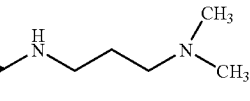
Racemic body
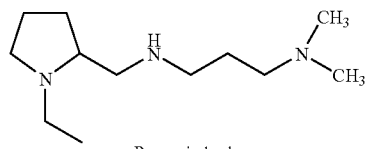
Racemic body
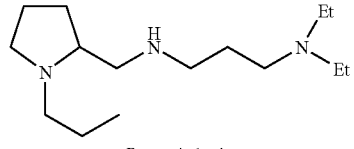
Racemic body
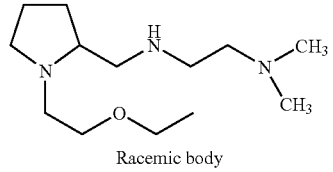
Racemic body
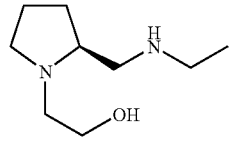
-continued
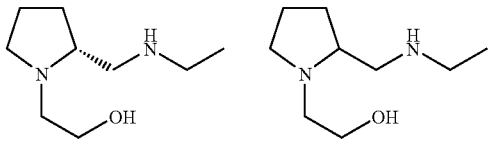
Racemic body
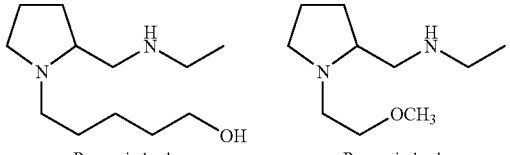
Racemic body
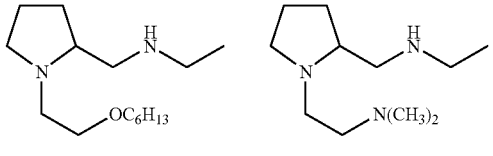
Racemic body
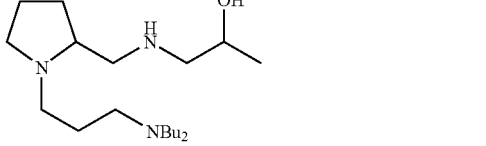
Racemic body
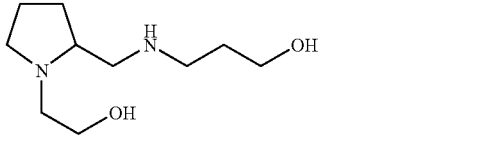
Racemic body
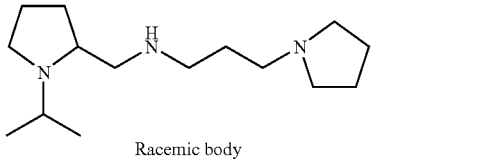
Racemic body
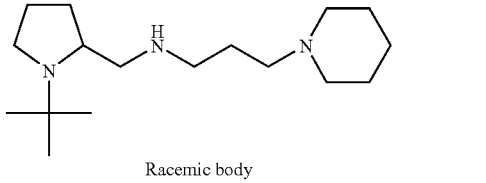
Racemic body
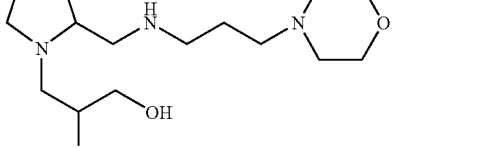
Diastereomer mixture
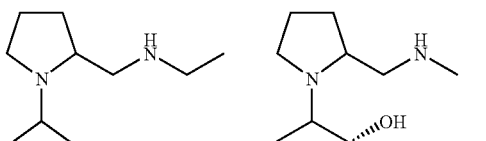
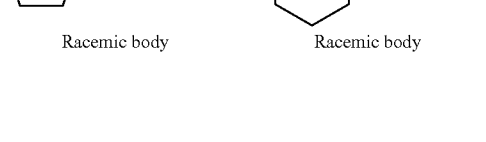
Racemic body    Racemic body

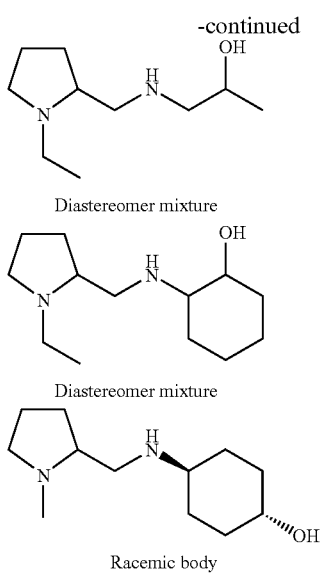

Preferred examples of the salt of the nitrogenous compound (Compound (1) or (2)) of the formula (1) or (2) include salts of an inorganic acid or organic acid such as hydrochloric acid, sulfuric acid, phosphoric acid, acetic acid, propionic acid, lactic acid, citric acid, succinic acid, hydrobromic acid, hydroiodic acid, methanesulfonic acid and perchloric acid.

As the compound (1) or (2) serving as component (a), two or more compounds may be used in combination and their content is not particularly limited. From the viewpoints of sufficient bleaching•hair dyeing effects, the content is preferably from 0.01 to 20 wt. %, more preferably from 0.02 to 10 wt. %, still more preferably from 0.05 to 8 wt. %, especially preferably from 0.1 to 5 wt. % in the whole composition composed of the first component part and the second component part.

As the oxidizing agent serving as Component (b), hydrogen peroxide and hydrogen peroxide generators such as urea peroxide, melamine peroxide, sodium perborate, potassium perborate, sodium percarbonate and potassium percarbonate can be given as examples, of which hydrogen peroxide is especially preferred. Its using amount can be selected as needed insofar as it does not cause the pH to exceed the required range. For example, from the viewpoints of sufficient bleaching•hair dyeing effects, and reduction of the hair damage or scalp irritation, the content of the oxidizing agent in terms of hydrogen peroxide is preferably from 0.1 to 12 wt. %, more preferably from 0.5 to 9 wt. %, especially preferably from 1 to 6 wt. % in the whole composition having the first and second component parts.

Examples of the alkali agent as the component (c) include ammonia, alkanolamines such as monoethanolamine, isopropanolamine, 2-amino-2-methylpropanol and 2-aminobutanol, alkanediamines such as 1,3-propanediamine, and carbonates such as ammonium carbonate, ammonium bicarbonate, guanidine carbonate, sodium carbonate, potassium carbonate, sodium bicarbonate and potassium bicarbonate. Of these, ammonia and alkanolamines are preferred. Of the alkanolamines, monoethanolamine is more preferred. As the alkali agent, two or more of the above-described ones may be used in combination. Its content can be selected as needed within a range satisfying the necessary pH. From the standpoints of providing sufficient bleaching•dyeing effect and also reducing hair damage and irritation to the scalp, the content of the alkali agent is preferably from 0.05 to 10 wt. %, more preferably from 0.1 to 5 wt. %, especially preferably from 0.2 to 3 wt. % in the whole composition composed of the first component part and the second component part.

The hair bleach composition or hair dye composition according to the present invention can bring about sufficient bleaching•dyeing effects without using ammonia as an alkali agent. Without any ammonia-derived irritating odor and unpleasant feeling during use, the composition is preferably employed.

In the hair bleach composition or hair dye composition of the present invention, a first component part containing an alkali agent and a second component part containing an oxidizing agent are mixed at a ratio ranging from 1:0.5 to 1:3 in terms of first component part:second component part (weight ratio) in consideration of practical utility.

The first component part and the second component part preferably have a pH of from 8 to 12 and from 2 to 5, respectively, at 25° C. The hair dye composition after mixture of the first and second component parts has a pH of from 7.5 to 12, but in view of the bleaching•hair dyeing effects and reduction in the skin irritation, the pH from 8 to 11 is preferred. As a pH regulator, in addition to the alkali agent as Component (c), an inorganic acid such as hydrochloric acid or phosphoric acid, an organic acid such as citric acid, glycolic acid or lactic acid, a hydrochloride salt such as ammonium chloride or monoethanolamine hydrochloride, or phosphate salt such as monopotassium dihydrogenphosphate or disodium monohydrogen phosphate can be used.

When the hair bleach composition or hair dye composition of the present invention further contains, as a chelating agent which is known to be used for hair bleaching and hair dye compositions, at least one selected from ethylenediaminetetraacetic acid, ethylenediaminehydroxyethyltriacetic acid, diethylenetriaminepentaacetic acid and salts thereof, the oxidizing agent and alkali agent act in the hair more efficiently. Addition of the chelating agent is therefore preferred. The content of the chelating agent preferably falls within a range of from 0.01 to 5 wt. % in the whole composition composed of the first component and second component parts from the viewpoints of sufficient bleaching•hair dyeing effects. The chelating agent can be incorporated in either one or both of the first and second component parts.

For the hair bleach or hair dye composition of the present invention, water and/or organic solvent is used as a medium. Examples of the organic solvent include lower alkanols such as ethanol and 2-propanol, aromatic alcohols such as benzyl alcohol and benzyloxyethanol, polyols such as propylene glycol, 1,3-butanediol, diethylene glycol and glycerin, cellosolves such as ethyl cellosolve, butyl cellosolve and benzyl cellosolve, and carbitols such as ethyl carbitol and butyl carbitol.

The hair dye composition of the present invention further contains, as Component (d), an intermediate for oxidation dye or a direct dye.

As such an intermediate for oxidation dye, known developers and couplers which are ordinarily employed for hair dyes can be used. Examples of the developer include paraphenylenediamine, toluene-2,5-diamine, 2-chloro-paraphenylenediamine, N-methoxyethyl-paraphenylenediamine, N,N-bis(2-hydroxyethyl)-paraphenylenediamine, 2-(2-hydroxyethyl)-paraphenylenediamine, 2,6-dimethyl-para-phenylenediamine, 4,4'-diaminodiphenylamine, 1,3-bis(N-(2-hydroxyethyl)-N-(4-aminophenyl)amino)-2-propanol, PEG-3,2,2'-paraphenylenediamine, paraminophenol, paramethylaminophenol, 3-methyl-4-aminophenol, 2-aminomethyl-4-aminophenol, 2-(2-hydroxyethylaminomethyl)-4-aminophenol, orthoaminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraminopyrimidine, 2,5,6-triamino-4-hydroxypyrimidine, 4,5-diamino-1-(4'-chlorobenzyl)pyrazole and 4,5-diamino-1-hydroxyethylpyrazole, and salts thereof.

Examples of the coupler include metaphenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, metaminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-metaaminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, and 2,6-diaminopyridine and salts thereof.

As each of the developer and coupler, they may be used in combination of two or more thereof. The content of the developer or coupler is preferably from 0.01 to 5 wt. %, especially preferably from 0.1 to 4 wt. % in the whole composition composed of first component and second component parts.

As the direct dye, on the other hand, known acidic dyes, basic dyes, disperse dyes, reactive dyes and the like, which can be used for hair dyes, can be used. The acidic dyes include Red No. 2 (C.I. 16185), Red No. 3 (C.I. 45430), Red No. 102 (C.I. 16255), Red No. 104 (1) (C.I. 45410), Red No. 105 (1) (C.I. 45440), Red No. 106 (C.I. 45100), Yellow No. 4 (C.I. 19140), Yellow No. 5 (C.I. 15985), Green No. 3 (C.I. 42053), Blue No. 1 (C.I. 42090), Blue No. 2 (C.I. 73015), Red No. 201 (C.I. 15850), Red No. 227 (C.I. 17200), Red No. 230 (1) (C.I. 45380), Red No. 231 (C.I. 45410), Red No. 232 (C.I. 45440), Orange No. 205 (C.I. 15510), Orange No. 207 (C.I. 45425), Yellow No. 202 (1) (C.I. 45350), Yellow No. 203 (C.I. 47005), Green No. 201 (C.I. 61570), Green No. 204 (C.I. 59040), Green No. 205 (C.I. 42095), Blue No. 202 (C.I. 42052), Blue No. 205 (C.I. 42090), Brown No. 201 (C.I. 20170), Red No. 401 (C.I. 45190), Red No. 502 (C.I. 16155), Red No. 503 (C.I. 16150), Red No. 504 (C.I. 14700), Red No. 506 (C.I. 15620), Orange No. 402 (C.I. 14600), Yellow No. 402 (C.I. 18950), Yellow No. 403 (1) (C.I. 10316), Yellow No. 406 (C.I. 13065), Yellow No. 407 (C.I. 18820), Green No. 401 (C.I. 10020), Green No. 402 (C.I. 42085), Violet No. 401 (C.I. 60730), Black No. 401 (C.I. 20470), Acid Black 52 (C.I. 15711), Acid Blue 1 (C.I. 42045), Acid Blue 3 (C.I. 42051), Acid Blue 62 (C.I. 62045), Acid Brown 13 (C.I. 10410), Acid Green 50 (C.I. 44090), Acid Orange 3 (C.I. 10385), Acid Orange 6 (C.I. 14270), Acid Red 14 (C.I. 14720), Acid Red 35 (C.I. 18065), Acid Red 73 (C.I. 27290), Acid Red 184 (C.I. 15685), and Brilliant Black 1 (C.I. 28440).

The basic dyes include Basic Blue 7 (C.I. 42595), Basic Black 16 (C.I. 12210), Basic Blue 22 (C.I. 61512), Basic Blue 26 (C.I. 44045), Basic Blue 99 (C.I. 56059), Basic Blue 117, Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 51, Basic Red 76 (C.I. 12245), Basic Red 118 (C.I. 12251:1), Basic Orange 31, Basic Yellow 28 (C.I. 48054), Basic Yellow 57 (C.I. 12719), Basic Yellow 87 and Basic Black 2 (C.I. 11825); basic dyes each having a quaternized nitrogen atom on a side chain of an aromatic ring as described in Japanese Patent Publication No. Sho 58-2204, Japanese Patent Application Laid-Open No. Hei 9-118832 and the like; and basic dyes as described in Japanese Language Laid-open Publication (PCT) No. Hei 10-502946, Japanese Patent Application Laid-Open No. Hei 10-182379, Japanese Patent Application Laid-Open No. Hei 11-349457 and the like.

Examples of direct dyes other than acidic dyes or basic dyes include 2-amino-3-nitrophenol, 2-amino-4-nitrophenol, 2-amino-5-nitrophenol, 4-amino-3-nitrophenol, 2-amino-6-chloro-4-nitrophenol, 4-hydroxypropylamino-3-nitrophenol, 3-nitro-para-hydroxyethylaminophenol, 2-nitro-para-phenylenediamine, 4-nitro-ortho-phenylenediamine, 4-nitro-meta-phenylenediamine, 6-nitro-ortho-toluidine, 6-nitro-para-toluidine, hydroxyethyl-2-nitro-para-toluidine, N,N'-bis(2-hydroxyethyl)-2-nitro-para-phenylenediamine, 2-chloro-5-nitro-N-hydroxyethyl-para-phenylenediamine, 2-nitro-5-glycerylmethylaniline, 3-methylamino-4-nitrophenoxyethanol, N-ethyl-3-nitroPABA, picramic acid, 2-hydroxyethylpicramic acid, 4-nitrophenylaminoethylurea, Violet No. 201 (C.I. 60725), Solvent Yellow 44 (C.I. 56200), Disperse Red 17 (C.I. 11210), Disperse Violet 1 (C.I. 61100), Disperse Violet 4 (C.I. 61105), Disperse Blue 3 (C.I. 61505), Disperse Blue 7 (C.I. 62500), HC Blue No. 2, HC Blue No. 8, HC Orange No. 1, HC Orange No. 2, HC Red No. 1, HC Red No. 3, HC Red No. 7, HC Red No. 8, HC Red No. 10, HC Red No. 11, HC Red No. 13, HC Red No. 16, HC Violet No. 2, HC Yellow No. 2, HC Yellow No. 5, HC Yellow No. 6, HC Yellow No. 7, HC Yellow No. 9, and HC Yellow No. 12.

These direct dyes may be used in combination of two or more thereof. Its content is preferably from 0.001 to 5 wt. %, especially preferably from 0.01 to 4 wt. % in the whole composition composed of the first component and second component parts. The oxidation dye and direct dye may be used in combination.

To the hair bleach composition or hair dye composition according to the present invention, ingredients commonly employed as cosmetic raw materials can be added, in addition to the above-described ingredients. Illustrative of such optional ingredients are hydrocarbons, animal or vegetable oils and fats, higher fatty acids, penetration enhancers, cationic surfactants, natural or synthetic polymers, higher alcohols, ethers, amphoteric surfactants, nonionic surfactants, protein derivatives, amino acids, antiseptics, chelating agents, stabilizers, antioxidants, plant extracts, crude drug extracts, vitamins, colorants, fragrances and ultraviolet absorbers.

The hair bleach composition or hair dye composition of the present invention is provided, similar to oxidation type hair bleaches or hair dyes widely employed now, as a two-part type having a first component part containing an alkali agent and a second component part containing an oxidizing agent. These first and second component parts can be provided in the form, for example, of liquid, emulsion, cream, gel, paste, or mousse. It may also be provided in the form of an aerosol. The mixture of the first component part and second component part has preferably a viscosity enough not to cause sagging when applied to the hair. It preferably has a viscosity of 2000 to 100000 mPa·s when measured at 25° C. by a Brookfield rotating viscometer. The viscosity here is a value measured after rotation using Rotor No. 3 for 1 minute at 12 rpm.

In order to bleach or dye the hair by using the hair bleach composition or hair dye composition of the present invention, it is only necessary to mix the first component part and second component part of the hair dye composition of the present invention, apply the mixture to the hair at 15 to 45° C., causing it to act on the hair for 1 to 60 minutes, preferably from 3 to 45 minutes, washing the hair and then drying.

EXAMPLES

Compounds used in Examples 1 to 32 are shown below.

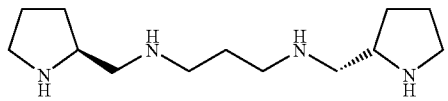

Compound (2-1)

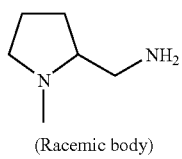

Compound (1-5)

(Racemic body)

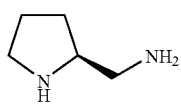

Compound (1-1)

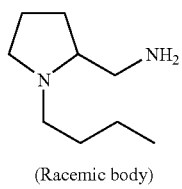

Compound (1-6)

(Racemic body)

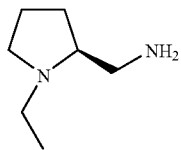

Compound (1-2)

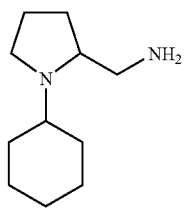

Compound (1-7)

(Racemic body)

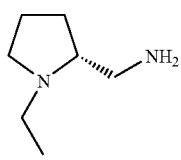

Compound (1-3)

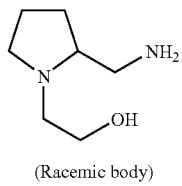

Compound (1-8)

(Racemic body)

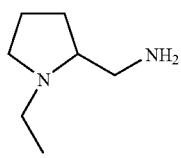

Compound (1-4)

(Racemic body)

Examples 1 to 9 and Comparative Examples 1 and 2

Oxidation type hair bleach compositions as shown in Table 2 were prepared in a conventional manner.

TABLE 2

| | | Examples | | | | | | | | | Comparative Examples | |
|---|---|---|---|---|---|---|---|---|---|---|---|---|
| | | 1 | 2 | 3 | 4 | 5 | 6 | 7 | 8 | 9 | 1 | 2 |
| First comp. part | 28 wt. % Aqueous ammonia | 8 | 8 | 8 | 8 | 8 | 8 | 8 | 8 | 8 | 8 | 8 |
| | Tetrasodium ethylenediaminetetra-acetate 4 hydrate | 0.125 | 0.125 | 0.125 | 0.125 | 0.125 | 0.125 | 0.125 | 0.125 | 0.125 | 0.125 | 0.125 |
| | Compound (1-1) | 0.4 | | | | | | | | | | |
| | Compound (1-2) | | 0.4 | | | | | | | | | |
| | Compound (1-3) | | | 0.4 | | | | | | | | |
| | Compound (1-4) | | | | 0.4 | | | | | | | |
| | Compound (2-1) | | | | | 0.4 | | | | | | |
| | Compound (1-5) | | | | | | 0.4 | | | | | |
| | Compound (1-6) | | | | | | | 0.4 | | | | |
| | Compound (1-7) | | | | | | | | 0.4 | | | |
| | Compound (1-8) | | | | | | | | | 0.4 | | |
| | Purified water | Balance | Balance | Balance | Balance | Balance | Balance | Balance | Balance | Balance | Balance | Balance |
| Second comp. part | 35 wt. % Aqueous hydrogen peroxide | 17.14 | 17.14 | 17.14 | 17.14 | 17.14 | 17.14 | 17.14 | 17.14 | 17.14 | 17.14 | 25.71 |
| | Purified water | Balance | Balance | Balance | Balance | Balance | Balance | Balance | Balance | Balance | Balance | Balance |

After 1 part by weight of the first component part was mixed with 1.5 parts of the second component part, the mixture was applied to the black hair of the Japanese (1 g tress). The mixture was caused to act on the hair for 30 minutes and then the hair was washed with a conventional shampoo, followed by drying. The color tone of the bleached hair was measured by a calorimeter of Konica Minolta and a difference in the hue from the untreated hair was observed. As a result, it has been found that in Examples 1 to 9, the bleaching property was better than in Comparative Example 1 and the bleaching property was comparable to that of Comparative Example 2. With regards to the touch of the hair after treatment, the bleached hair with the composition of Comparative Example 2 was damaged severely, but the bleached hair with any one of the compositions of Examples 1 to 9 was only slightly damaged and its degree was comparable to that of Comparative Example 1.

Examples 10 to 14 and Comparative Examples 3 to 4

In a conventional manner, oxidation type hair bleach compositions as shown in Table 3 were prepared.

TABLE 3

| | | Examples | | | | | Comparative Examples | |
|---|---|---|---|---|---|---|---|---|
| | | 10 | 11 | 12 | 13 | 14 | 3 | 4 |
| First Comp. part | Monoethanolamine | 5 | 5 | 5 | 5 | 5 | 5 | 5 |
| | Tetrasodium EDTA tetrahydrate | 0 | 0 | 0 | 0 | 0 | 0 | 0 |
| | Compound (1-1) | 0.4 | | | | | | |
| | Compound (1-2) | | 0.4 | | | | | |
| | Compound (1-3) | | | 0.4 | | | | |
| | Compound (1-4) | | | | 0.4 | | | |
| | Compound (2-1) | | | | | 0.4 | | |
| | Purified water | Balance | Balance | Balance | Balance | Balance | Balance | Balance |
| Second Comp. part | 35 wt. % Aqueous hydrogen peroxide | 17.14 | 17.14 | 17.14 | 17.14 | 17.14 | 17.14 | 25.71 |
| | Purified water | Balance | Balance | Balance | Balance | Balance | Balance | Balance |

In a similar manner to Examples 1 to 9, bleaching, washing and drying were conducted and the color tone of the bleached hair was measured. A difference in the color hue from the untreated hair was observed. As a result, the bleaching property of the hair treated with any one of the compositions in Examples 10 to 14 was superior to that in Comparative Example 3 and was comparable to that in Comparative Example 4. With regards to the touch of the hair, the hair bleached with the composition of Comparative Example 4 was damaged severely, while the damage of the hair treated with any one of the compositions in Examples 10 to 14 was as week as that treated with the composition obtained in Comparative Example 3.

Examples 15 to 24

In a conventional manner, oxidation type hair bleach compositions as shown in Tables 4 and 5 were prepared.

TABLE 4

|  |  | Examples | | | | |
|---|---|---|---|---|---|---|
|  |  | 15 | 16 | 17 | 18 | 19 |
| First comp. part | Compound (1-2) | 0.1 | 2 | | | |
|  | Compound (1-3) | | | 1 | | |
|  | Compound (1-4) | | | | 1 | |
|  | Compound (2-1) | | | | | 1 |
|  | 28 wt. % Aqueous ammonia | 6 | | 6 | 3 | |
|  | Monoethanolamine | | 5 | | 3 | 5 |
|  | Propylene glycol | 10 | 10 | 2 | 2 | 2 |
|  | Ethanol | 15 | 15 | | | |
|  | Polyoxyethylene (20) octyldodecyl ether | 10 | 10 | | | |
|  | Polyoxyethylene (40) cetyl ether | | | 2 | 2 | 2 |
|  | Polyoxyethylene (2) cetyl ether | | | 2.5 | 2.5 | 2.5 |
|  | Oleic acid diethanolamide | 8 | 8 | | | |
|  | Oleyl alcohol | 2 | 2 | | | |
|  | Stearyl trimethylammonium chloride | | | 1.5 | 1.5 | 1.5 |
|  | Cetanol | | | 1 | 1 | 1 |
|  | Liquid paraffin | | | 0.5 | 0.5 | 0.5 |
|  | Ammonium chloride | q.s.[a] | q.s.[a] | q.s.[a] | q.s.[a] | q.s.[a] |
|  | Purified water | Balance | Balance | Balance | Balance | Balance |
| Second comp. part | Hydrogen peroxide | 6 | 3 | 3 | 6 | 9 |
|  | Methylparaben | 0.1 | 0.1 | 0.1 | 0.1 | 0.1 |
|  | Phosphoric acid | q.s.[b] | q.s.[b] | q.s.[b] | q.s.[b] | q.s.[b] |
|  | Purified water | Balance | Balance | Balance | Balance | Balance |

[a] amount to adjust the pH to 9.8
[b] amount to adjust the pH to 3.5

TABLE 5

|  |  | Examples | | | | |
|---|---|---|---|---|---|---|
|  |  | 20 | 21 | 22 | 23 | 24 |
| First comp. part | Compound (1-1) | 0.1 | 2 | | | |
|  | Compound (1-2) | | | 1 | | |
|  | Compound (1-4) | | | | 1 | |
|  | Compound (2-1) | 0.1 | | | | 1 |
|  | Tetrasodium ethylenediaminetetraacetate tetrahydrate | | 1 | 0.5 | | |
|  | Trisodium ethylenediaminehydroxyethyltriacetate | | | | 2 | |
|  | Pentasodium Diethylenetriaminepentaacetate | | | | | 1 |
|  | 28 wt. % Aqueous ammonia | 6 | | 6 | 3 | |
|  | Monoethanolamine | | 5 | | 3 | 5 |
|  | Propylene glycol | 10 | 10 | 2 | 2 | 2 |
|  | Ethanol | 15 | 15 | | | |
|  | Polyoxyethylene (20) octyldodecyl ether | 10 | 10 | | | |
|  | Polyoxyethylene (40) cetyl ether | | | 2 | 2 | 2 |
|  | Polyoxyethylene (2) cetyl ether | | | 2.5 | 2.5 | 2.5 |
|  | Oleic acid diethanolamide | 8 | 8 | | | |
|  | Oleyl alcohol | 2 | 2 | | | |
|  | Stearyltrimethylammonium chloride | | | 1.5 | 1.5 | 1.5 |
|  | Cetanol | | | 1 | 1 | 1 |
|  | Liquid paraffin | | | 0.5 | 0.5 | 0.5 |
|  | Ammonium chloride | q.s.[a] | q.s.[a] | q.s.[a] | q.s.[a] | q.s.[a] |
|  | Purified water | Balance | Balance | Balance | Balance | Balance |
| Second comp. part | Hydrogen peroxide | 6 | 3 | 3 | 6 | 9 |
|  | Methyparaben | 0.1 | 0.1 | 0.1 | 0.1 | 0.1 |
|  | Phosphoric acid | q.s.[b] | q.s.[b] | q.s.[b] | q.s.[b] | q.s.[b] |
|  | Purified water | Balance | Balance | Balance | Balance | Balance |

[a] amount to adjust the pH to 9.8
[b] amount to adjust the pH to 3.5

In a similar manner to Examples 1 to 9 except for the use of 1 part by weight of the second component part relative to 1 part by weight of the first component part, bleaching, washing and drying were conducted. The color tone of the bleached hair was measured and a difference in color hue from the untreated hair was observed. As a result, the bleaching property of the hair treated with any one of the compositions obtained in Examples 20 to 24 was superior to that of a composition to which any one of the compounds (1-2), (1-3), (1-4) and (2-1) had not been added.

Examples 25 to 32

In a conventional manner, oxidation type hair dyes as shown in Tables 6 and 7 were prepared.

TABLE 6

| | | Examples | | | |
|---|---|---|---|---|---|
| | | 25 | 26 | 27 | 28 |
| First Comp. Part | Compound (1-2) | 0.1 | | | |
| | Compound (1-3) | | 1 | | |
| | Compound (1-4) | | | 1 | |
| | Compound (2-1) | 0.1 | | | 1 |
| | Tetrasodium ethylenediaminetetraacetate tetrahydrate | | 0.5 | | |
| | Trisodium ethylenediaminehydroxyethyltriacetate | | | 2 | |
| | Pentasodium diethylenetriaminepentaacetate | | | | 1 |
| | Toluene-2,5-diamine | 1.9 | 1.9 | 1 | |
| | Para-aminophenol | | | | 1 |
| | Resorcin | 2 | 2 | | |
| | Para-aminoorthocresol | | | | 1.1 |
| | 2,4-Diaminophenoxyethanol | | | 1.37 | |
| | 28 wt. % Aqueous ammonia | 5 | 5 | 5 | 5 |
| | Monoethanolamine | 2 | 2 | 2 | 2 |
| | Propylene glycol | 8 | 8 | 8 | 8 |
| | Polyoxyethylene (20) isostearyl ether | 24 | 24 | 24 | 24 |
| | Polyoxyethylene (2) isostearyl ether | 20 | 20 | 20 | 20 |
| | Merquat (product of Calgon, 35 wt. % aq. soln.) | 8 | 8 | | |
| | Polymer JR400 (product of Union Carbide) | | | 0.5 | |
| | Amodimethicone SM8702C (product of Dow Corning Toray Silicone) | | | | 2 |
| | Sodium sulfite | 0.05 | 0.05 | 0.05 | 0.05 |
| | Ascorbic acid | 0.5 | 0.5 | 0.5 | 0.5 |
| | Fragrance | q.s. | q.s. | q.s. | q.s. |
| | Ammonium chloride | q.s.[c] | q.s.[c] | q.s.[c] | q.s.[c] |
| | Purified water | Balance | Balance | Balance | Balance |
| Second comp. part | Hydrogen peroxide | 6 | 3 | 3 | 3 |
| | Methylparaben | 0.5 | 0.5 | 0.5 | 0.5 |
| | Phosphoric acid | q.s.[d] | q.s.[d] | q.s.[d] | q.s.[d] |
| | Purified water | Balance | Balance | Balance | Balance |

[a] amount to adjust the pH to 10
[b] amount to adjust the pH to 3.5

TABLE 7

| | | Examples | | | |
|---|---|---|---|---|---|
| | | 29 | 30 | 31 | 32 |
| First Comp. Part | Compound (1-2) | 0.1 | | | |
| | Compound (1-3) | | 1 | | |
| | Compound (1-4) | | | 1 | |
| | Compound (2-1) | 0.1 | | | 1 |
| | Tetrasodium ethylenediaminetetraacetate tetrahydrate | | 0.5 | | |
| | Trisodium ethylenediaminehydroxyethyltriacetate | | | 2 | |
| | Pentasodium Diethylenetriaminepentaacetate | | | | 1 |
| | Toluene-2,5-diamine | | | 1.9 | |
| | Para-aminophenol | | | | 1 |
| | Resorcin | | | 2 | |
| | Para-aminoorthocresol | | | | 1.1 |
| | 2,4-Diaminophenoxyethanol | | | 1.37 | |
| | Basic Red 12 | 0.2 | 0.2 | | |
| | Basic Red 76 | 0.1 | | 0.2 | |
| | HC Red 3 | | 0.1 | | 0.2 |
| | Monoethanolamine | 5 | 5 | 5 | 5 |
| | Propylene glycol | 8 | 8 | 8 | 8 |
| | Polyoxyethylene (20) isostearyl ether | 24 | 24 | 24 | 24 |
| | Polyoxyethylene (2) isostearyl ether | 20 | 20 | 20 | 20 |
| | Merquat (product of Calgon, 35 wt. % aq. soln.) | 8 | 8 | | |
| | Polymer JR400 (product of Union Carbide) | | | 0.5 | |

TABLE 7-continued

|  |  | Examples | | | |
|---|---|---|---|---|---|
|  |  | 29 | 30 | 31 | 32 |
|  | Amodimethicone SM8702C (product of Dow Corning Toray Silicone) |  |  |  | 2 |
|  | Sodium sulfite | 0.05 | 0.05 | 0.05 | 0.05 |
|  | Ascorbic acid | 0.5 | 0.5 | 0.5 | 0.5 |
|  | Fragrance | q.s. | q.s. | q.s. | q.s. |
|  | Ammonium chloride | q.s.[c] | q.s.[c] | q.s.[c] | q.s.[c] |
|  | Purified water | Balance | Balance | Balance | Balance |
| Second comp. part | Hydrogen peroxide | 6 | 3 | 3 | 3 |
|  | Methylparaben | 0.5 | 0.5 | 0.5 | 0.5 |
|  | Phosphoric acid | q.s.[d] | q.s.[d] | q.s.[d] | q.s.[d] |
|  | Purified water | Balance | Balance | Balance | Balance |

[a] amount to adjust the pH to 10
[b] amount to adjust the pH to 3.5

After 1 part by weight of the first component part was mixed with 1.5 parts by weight of the second component part, the mixture was applied to the black hair (1 g) of the Japanese at 30° C. The mixture was allowed to act on the hair for 30 minutes, followed by washing with a conventional shampoo and drying. The color tone of the hair thus dyed was measured by a calorimeter of Konica Minolta and a difference in the color hue from the untreated hair was observed. As a result, the hair treated with any one of the compositions obtained in Examples 25 to 32 was superior to that treated with the composition to which any one of the compound (1-2), (1-3), (1-4) and (2-1) had not been added.

Examples 33 to 40 and Comparative Examples 5 and 6

Compounds used in Examples 33 to 40 are shown below:

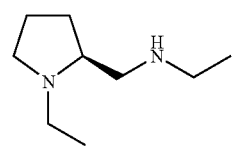

Compound A

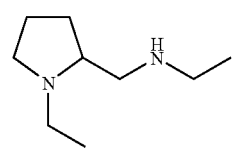

Compound B

Racemic body

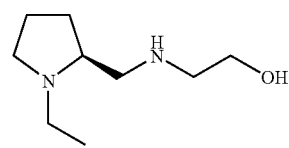

Compound C

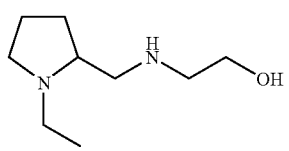

Compound D

Racemic body

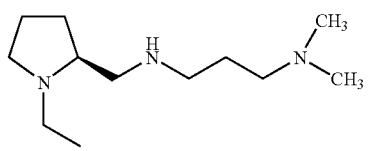

Compound E

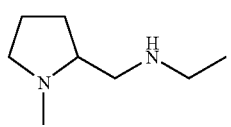

Compound F

Racemic body

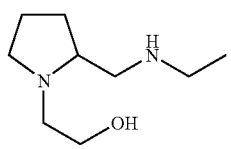

Compound G

Racemic body

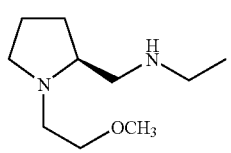

Compound H

Racemic body

The oxidation type hair bleach compositions as shown in Table 8 were prepared.

TABLE 8

| | | Examples | | | | | | | | Comp. Ex. | |
| --- | --- | --- | --- | --- | --- | --- | --- | --- | --- | --- | --- |
| | | 33 | 34 | 35 | 36 | 37 | 38 | 39 | 40 | 5 | 6 |
| First comp. part | 28 wt. % aqueous ammonia | 8 | 8 | 8 | 8 | 8 | 8 | 8 | 8 | 8 | 8 |
| | Tetrasodium ethylenediaminetetraacetate tetrahydrate | 0.125 | 0.125 | 0.125 | 0.125 | 0.125 | 0.125 | 0.125 | 0.125 | 0.125 | 0.125 |
| | Compound A | 0.4 | | | | | | | | | |
| | Compound B | | 0.4 | | | | | | | | |
| | Compound C | | | 0.4 | | | | | | | |
| | Compound D | | | | 0.4 | | | | | | |
| | Compound E | | | | | 0.4 | | | | | |
| | Compound F | | | | | | 0.4 | | | | |
| | Compound G | | | | | | | 0.4 | | | |
| | Compound H | | | | | | | | 0.4 | | |
| | Purified water | Balance | Balance | Balance | Balance | Balance | Balance | Balance | Balance | Balance | Balance |
| Second comp. Part | 35 wt. % aqueous hydrogen peroxide | 17.14 | 17.14 | 17.14 | 17.14 | 17.14 | 17.14 | 17.14 | 17.14 | 17.14 | 25.71 |
| | Purified water | Balance | Balance | Balance | Balance | Balance | Balance | Balance | Balance | Balance | Balance |

After 1 part by weight of the first component part was mixed with 1.5 parts by weight of the second component part, the mixture was applied to the black hair (1 g tress) of the Japanese at 30° C. The mixture was allowed to act on the hair for 30 minutes, followed by washing with a conventional shampoo and drying. The color tone of the hair thus dyed was measured by a colorimeter of Konica Minolta and a difference in the color hue from the untreated hair was observed. As a result, the hair treated with any one of the compositions obtained in Examples 33 to 40 was superior in bleaching property to that treated with the composition obtained in Comparative Example 5 and was comparable to Comparative Example 6.

INDUSTRIAL APPLICABILITY

The hair dye composition of the present invention has excellent bleaching power, is capable of dyeing the hair with a bright color tone and good color hue and is less damaging to the hair and less irritating to the scalp.

The invention claimed is:

1. A hair bleach composition to be used after mixing a first component part containing an alkali agent and a second component part containing an oxidizing agent, which comprises, after mixing, the following components (a) to (c):

(a) a nitrogenous compound represented by the following formula (1) or (2), or salt thereof:

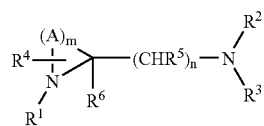

(1)

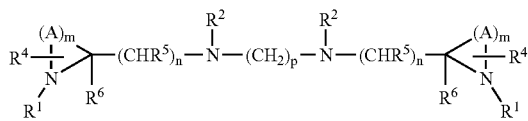

(2)

(wherein, one or two of As each represents $CH_2$ which may be substituted by one or two selected from O, S and NH, $R^1$ represents a hydrogen atom; an alkyl, cycloalkyl or alkenyl group which has 12 or less carbon atoms and may be substituted by at least one group selected from a hydroxy group, an amino group which may be substituted by at least one alkyl group, an amide group which may be substituted by at least one alkyl group, a $C_{1-6}$ (poly)alkoxy or benzyloxy group which may be substituted by a hydroxy group or an amino group, a thioether group and an ester group; an alkyl halide group; or a benzyl, pyridylmethyl or phenyl group which may be substituted by at least one halogen atom;

$R^2$ and $R^3$ each represents a hydrogen atom; an alkyl, alkenyl or cycloalkyl group which has 12 or less carbon atoms and may substituted by at least one group selected from hydroxy group, amino group which may be substituted by at least one alkyl group and $C_{1-6}$ alkoxy group; an acyl group having 12 or less carbon atoms; an alkylsulfonyl group having 12 or less carbon atoms; or a phenylsulfonyl group which may be substituted by at least one alkyl group; or $R^2$ and $R^3$ may form a 4- to 7-membered ring cyclic amino group together with a nitrogen atom adjacent thereto, $R^4$, $R^5$ and $R^6$ each represents a hydrogen atom; a hydroxy group; an amino group; an alkyl ether group; or an alkyl or alkenyl group which has 12 or less carbon atoms and may be substituted by at least one group selected from a hydroxy group, and an amino group which may be substituted by at least one alkyl group, m stands for an integer of from 2 to 5, n stands for an integer of from 1 to 4 and p stands for an integer of from 2 to 6, (b) an oxidizing agent; and (c) an alkali agent; and has, after mixing, a pH of from 7.5 to 12.

2. The hair bleach composition of claim 1 comprising ethylenediaminetetraacetic acid, ethylenediaminehydroxyethyltriacetic acid or diethylenetriaminepentaacetic acid or salt thereof.

3. A hair dye composition to be used after mixing a first component part containing an alkali agent and a second component part containing an oxidizing agent, which comprises, after mixing, comprises the following components (a) to (d):

(a) a nitrogenous compound represented by the following formula (1) or (2):

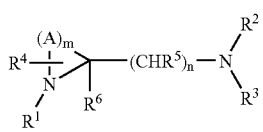

(1)

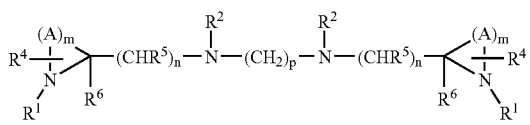

(2)

(wherein, one or two of As each represents $CH_2$ which may be substituted by one or two selected from O, S and NH, $R^1$ represents a hydrogen atom; an alkyl, cycloalkyl or alkenyl group which has 12 or less carbon atoms and may be substituted by at least one group selected from a hydroxy group, an amino group which may be substituted by at least one alkyl group, an amide group which may be substituted by at least one alkyl group, a $C_{1-6}$ (poly)alkoxy or benzyloxy group which may be substituted by a hydroxy or amino group, a thioether group and an ester group; an alkyl halide group; or a benzyl, pyridylmethyl or phenyl group which may be substituted by at least one halogen atom;

$R^2$ and $R^3$ each represents a hydrogen atom; an alkyl, alkenyl or cycloalkyl group which has 12 or less carbon atoms and may substituted by at least one group selected from hydroxy group, amino group which may be substituted by at least one alkyl group and $C_{1-6}$ alkoxy group; an acyl group having 12 or less carbon atoms; an alkylsulfonyl group having 12 or less carbon atoms; or a phenylsulfonyl group which may be substituted by at least one alkyl group; or $R^2$ and $R^3$ may form a 4- to 7-membered ring cyclic amino group together with a nitrogen atom adjacent thereto, $R^4$, $R^5$ and $R^6$ each represents a hydrogen atom; a hydroxy group; an amino group; an alkyl ether group; or an alkyl or alkenyl group which has 12 or less carbon atoms and may be substituted by at least one group selected from a hydroxy group, and an amino group which may be substituted by at least one alkyl group, m stands for an integer of from 2 to 5, n stands for an integer of from 1 to 4 and p stands for an integer of from 2 to 6, or salt thereof, (b) an oxidizing agent;

(c) an alkali agent; and (d) an intermediate for oxidation dye, or a direct dye; and has, after mixing, a pH of from 7.5 to 12.

4. The hair dye composition of claim 3 further comprising ethylenediaminetetraacetic acid, ethylenediaminehydroxyethyltriacetic acid or diethylenetriaminepentaacetic acid or salt thereof.

5. A hair treatment additive which comprises a nitrogenous compound represented by the following formula (1) or (2):

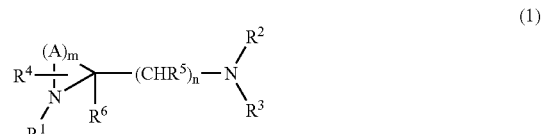

(1)

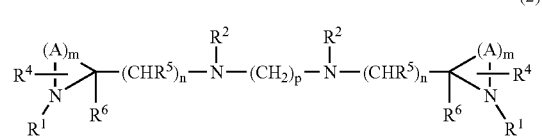

(2)

(wherein, one or two of As each represents $CH_2$ which may be substituted by one or two selected from O, S and NH, $R^1$ represents a hydrogen atom; an alkyl, cycloalkyl or alkenyl group which has 12 or less carbon atoms and may be substituted by at least one group selected from a hydroxy group, an amino group which may be substituted by at least one alkyl group, an amide group which may be substituted by at least one alkyl group, a $C_{1-6}$ (poly)alkoxy or benzyloxy group which may be substituted by a hydroxy group or an amino group, a thioether group and an ester group; an alkyl halide group; or a benzyl, pyridylmethyl or phenyl group which may be substituted by at least one halogen atom;

$R^2$ and $R^3$ each represents a hydrogen atom; an alkyl, alkenyl or cycloalkyl group which has 12 or less carbon atoms and may substituted by at least one group selected from hydroxy group, amino group which may be substituted by at least one alkyl group and $C_{1-6}$ alkoxy group; an acyl group having 12 or less carbon atoms; an alkylsulfonyl group having 12 or less carbon atoms; or a phenylsulfonyl group which may be substituted by at least one alkyl group; or $R^2$ and $R^3$ may form a 4- to 7-membered ring cyclic amino group together with a nitrogen atom adjacent thereto, $R^4$, $R^5$ and $R^6$ each represents a hydrogen atom; a hydroxy group; an amino group; an alkyl ether group; or an alkyl or alkenyl group which has 12 or less carbon atoms and may be substituted by at least one group selected from a hydroxy group, and an amino group which may be substituted by at least one alkyl group, m stands for an integer of from 2 to 5, n stands for an integer of from 1 to 4 and p stands for an integer of from 2 to 6); or salt thereof.

6. The hair bleach composition of claim 1, wherein in formulas (1) and (2) of component (a) A=$CH_2$.

7. The hair bleach composition of claim 6 wherein m=3.

8. The hair bleach composition of claim 7 wherein $R^5$=H.

9. The hair bleach composition of claim 8 wherein n=1.

10. The hair bleach composition of claim 9 wherein $R^2$=H.

11. The hair bleach composition of claim 10 wherein $R^1$ represents methyl, ethyl, propyl, butyl, cyolohexyl, hydroxyethyl or aminoethyl.

12. The hair bleach composition of claim 11 wherein $R^3=H$.

13. The hair bleach composition of claim 1, wherein in formulas (1) and (2) of component (a), $R^1$, $R^2$, $R^3$, $R^4$, $R^5$ and $R^6$ are, independent of one another, represented by hydrogen, methyl and ethyl groups.

14. The hair bleach composition of claim 13 wherein $R^6=H$.

15. The hair bleach composition of claim 1, wherein in formulas (1) and (2) of component (a), the cyclic nitrogen is tertiary.

16. The hair bleach composition of claim 1, wherein component (a) is at least one selected from the group consisting of 2-aminoethyl-1-methylpyrrolidine, 2-aminomethyl-1-ethylpyrrolidine, 2-aminomethyl-1-butylpyrrolidine, 2-aminomethyl-1-hydroxyethylpyrrolidine and 1-ethyl-2-(N-hydroxyethyl)aminomethylpyrrolidine.

17. The hair bleach composition of claim 1, wherein component (a) is at least one selected from the group consisting of Compounds 1-1, 1-2, 1-3, 1-4, 1-5, 1-6, 1-7, 1-8 and 2-1.

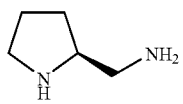

Compound (1-1)

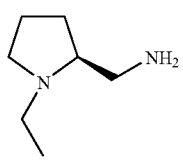

Compound (1-2)

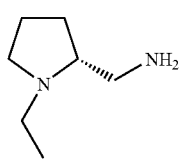

Compound (1-3)

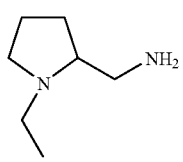

Compound (1-4)

(Racemic body)

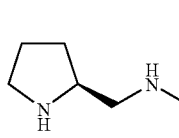

Compound (2-1)

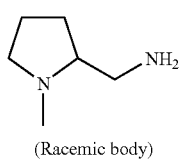

Compound (1-5)

(Racemic body)

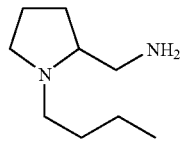

Compound (1-6)

(Racemic body)

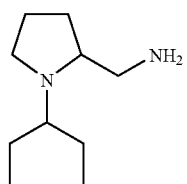

Compound (1-7)

(Racemic body)

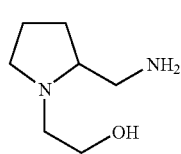

Compound (1-8)

(Racemic body)

18. The hair dye composition of claim 3, wherein in formulas (1) and (2) of component (a) $A=CH_2$.

19. The hair dye composition of claim 18 wherein $m=3$.

20. The hair dye composition of claim 19 wherein $R^5=H$.

21. The hair dye composition of claim 20 wherein $n=1$.

22. The hair dye composition of claim 21 wherein $R^2=H$.

23. The hair dye composition of claim 22 wherein $R^1$ represents methyl, ethyl, propyl, butyl, cyclohexyl, hydroxyethyl or aminoethyl.

24. The hair dye composition of claim 23 wherein $R^3=H$.

25. The hair dye composition of claim 3, wherein in formulas (1) and (2) of component (a), $R^1$, $R^2$, $R^3$, $R^4$, $R^5$ and $R^6$ are, independent of one another represented by hydrogen, methyl and ethyl groups.

26. The hair dye composition of claim 25 wherein $R^6=H$.

27. The hair dye composition of claim 3, wherein in formulas (1) and (2) of component (a) the cyclic nitrogen is tertiary.

28. The hair dye composition of claim 3, wherein component (a) is at least one selected from the group consisting of 2-aminoethyl-1-methylpyrrolidine, 2-aminomethyl-1-ethylpyrrolidine, 2-aminomethyl-1-butylpyrrolidine, 2-aminomethyl-1-hydroxyethylpyrrolidine and 1-ethyl-2-(N-hydroxyethyl)aminomethylpyrrolidine.

29. The hair dye composition of claim 3, wherein component (a) is at least one selected from the group consisting of Compounds 1-1, 1-2, 1-3, 1-4, 1-5, 1-6, 1-7, 1-8 and 2-1.

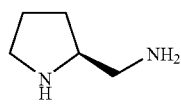

Compound (1-1)

-continued

Compound (1-2)

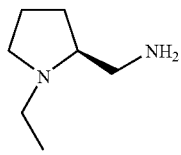

(Racemic body)

Compound (1-3)

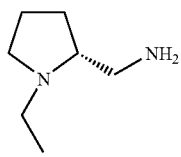

(Racemic body)

Compound (1-4)

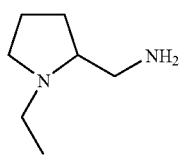

(Racemic body)

Compound (2-1)

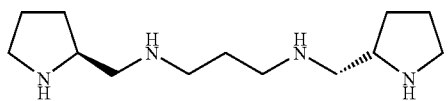

Compound (1-5)

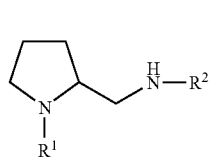

(Racemic body)

-continued

Compound (1-6)

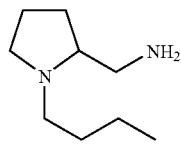

(Racemic body)

Compound (1-7)

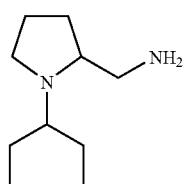

(Racemic body)

Compound (1-8)

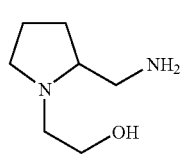

(Racemic body)

30. A hair treatment additive according to claim 5, which comprises a nitrogenous compound represented by the following formula (1b):

$$\text{(Ib)}$$

where $R^1$ and $R^2$ each represents a $C_{1-6}$ alkyl or $C_{3-6}$ cycloalkyl group which may be substituted by at least one group selected from hydroxy group, tertiary amino groups and $C_{1-6}$ alkoxy groups.

* * * * *

UNITED STATES PATENT AND TRADEMARK OFFICE
CERTIFICATE OF CORRECTION

PATENT NO. : 7,211,116 B2 Page 1 of 1
APPLICATION NO. : 10/497538
DATED : May 1, 2007
INVENTOR(S) : Akira Kiyomine et al.

It is certified that error appears in the above-identified patent and that said Letters Patent is hereby corrected as shown below:

Column 33, line 14, delete the word "comprises" following the phrase "after mixing."

Signed and Sealed this

Fourth Day of December, 2007

JON W. DUDAS
*Director of the United States Patent and Trademark Office*